United States Patent
Cunkelman et al.

(10) Patent No.: US 6,793,146 B2
(45) Date of Patent: Sep. 21, 2004

(54) BATTERY POWERED HUMIDITY INDICATOR

(75) Inventors: Brian L. Cunkelman, Blairsville, PA (US); Matthew D. Mitsch, Pittsburgh, PA (US)

(73) Assignee: Westinghouse Air Brake Technologies Corporation, Wilmerding, PA (US)

( * ) Notice: Subject to any disclaimer, the term of this patent is extended or adjusted under 35 U.S.C. 154(b) by 0 days.

(21) Appl. No.: 10/318,491

(22) Filed: Dec. 13, 2002

(65) Prior Publication Data

US 2004/0112972 A1 Jun. 17, 2004

(51) Int. Cl.$^7$ .............................................. F24F 11/00
(52) U.S. Cl. ..................... 236/44 A; 236/94; 62/129; 73/29.01
(58) Field of Search .................. 236/44 A, 94, 236/44 C; 62/129; 73/29.01, 29.02; 34/80

(56) References Cited

U.S. PATENT DOCUMENTS

| | | | | |
|---|---|---|---|---|
| 4,208,910 A | * | 6/1980 | Lezius ........................... | 73/336 |
| 4,801,211 A | * | 1/1989 | Yagi et al. ..................... | 374/28 |
| 4,915,816 A | * | 4/1990 | Shakkottai et al. .......... | 204/430 |
| 5,255,556 A | * | 10/1993 | Lobdell ........................ | 73/31.02 |
| 5,428,964 A | * | 7/1995 | Lobdell ........................ | 62/176.6 |
| 5,456,104 A | * | 10/1995 | Rosen ......................... | 73/29.02 |
| 5,677,476 A | * | 10/1997 | McCarthy et al. .......... | 73/29.01 |
| 6,629,420 B2 | * | 10/2003 | Renders ...................... | 62/129 |
| 2003/0103867 A1 | * | 6/2003 | Newman et al. .............. | 422/58 |

* cited by examiner

Primary Examiner—Marc Norman
(74) Attorney, Agent, or Firm—James Ray & Associates

(57) ABSTRACT

The present invention provides an apparatus that is used to measure relative humidity, such apparatus comprises a housing having a first end and a second end. There is a humidity sensor disposed at the first end of the housing for measuring the humidity in the air and a temperature sensor also disposed at the first end of the housing for measuring ambient temperature. The apparatus has an electronics portion in direct electrical communication with the humidity sensor and the temperature sensor for computing a relative humidity and a dewpoint temperature. The electronics portion is disposed within a center portion of the housing. There is, further, a battery that is in electrical communication with the electronics portion, the humidity sensor and the temperature sensor for providing power to the apparatus. Such battery is disposed in the center portion of the housing of the apparatus. The apparatus has a display means that is in electrical communication with the electronics portion and with the battery for displaying such relative humidity and such dew point temperature as determined by the electronics portion. The display means is disposed at a second end of said housing.

20 Claims, 2 Drawing Sheets

BATTERY POWERED HUMIDITY INDICATOR

FIELD OF THE INVENTION

The present invention relates, in general, to a means for measuring relative humidity and, more particularly, the present invention relates to a battery powered humidity indicator.

BACKGROUND OF THE INVENTION

Air dryers are used routinely in the railroad industry to provide clean, dry compressed air to locomotive and train air systems. Not only are air dryers used within the railroad industry but they are also widely used throughout other parts of general industry for similar purposes as with the railroad industry, that is, to provide dry, clean air. Some examples of air drying systems are found in U.S. Pat. No. 5,961,698 and U.S. Pat. No. 5,715,621. These patents are assigned to the Assignee of the present invention and their teachings are incorporated into the present document by reference thereto. In order to be certain that an air dryer is functioning properly it is necessary to measure the relative humidity of both the atmospheric air that enters the air dryer and the air exiting the air dryer that supplies such compressed air systems.

Generally, humidity measurements have been made in many of the commercial air drying systems by the use of a dyed paper which determines the an increase in humidity by a change in the paper color. Such a system, although functional, leaves a lot to be desired. One major problem with such dyed paper systems is that the paper is not regenerative in that it loses its ability to change color after a period of time. This is particularly true if the paper is exposed to very high humid air, in which case the dye in the paper may be essentially washed out and thus the paper can no longer give an indication of humidity.

Another drawback to the present system is that the paper is very slow to respond which can create problems. This is particularly true with today's rapid pace in virtually everything where results are expected instantly. Such slow response time is compounded by the fact that the dyed paper system is also relatively inaccurate. Generally, the accuracy of the dyed paper system is in the order of ±25 percent.

Thus, it would appear advantageous not only for use in air drying systems but for any measurement of relative humidity if a rapid, accurate, regenerative system were developed.

SUMMARY OF THE INVENTION

The present invention provides an apparatus that is used to measure relative humidity, such apparatus comprises a housing having a first end and a second end. There is a humidity sensor disposed at the first end of the housing for measuring the humidity in the air and a temperature sensor also disposed at the first end of the housing for measuring ambient temperature. The apparatus has an electronics portion in direct electrical communication with the humidity sensor and the temperature sensor for computing a relative humidity and a dewpoint temperature. The electronics portion is disposed within a center portion of the housing. There is, further, a battery that is in electrical communication with the electronics portion, the humidity sensor and the temperature sensor for providing power to the apparatus. Such battery is disposed in the center portion of the housing of the apparatus. The apparatus has a display means that is in electrical communication with the electronics portion and with the battery for displaying such relative humidity and such dew point temperature as determined by the electronics portion. The display means is disposed at a second end of said housing.

In an alternate embodiment of the invention there is provided in combination with an air drying system having a first housing member, an air inlet manifold and an air outlet manifold disposed in the first housing member, a pair of towers disposed in the first housing, a first one of a pair of towers serving as a drying tower fluidly connected to the air inlet manifold and the air outlet manifold whenever a second one of the pair of towers is being regenerated and the second one of the pair of towers serving as a drying tower when the first one of the pair of towers is being regenerated, the improvement comprises at least one apparatus disposed in the housing for measuring humidity. The at least one apparatus is fluidly connected to the air inlet manifold, the air outlet manifold and the at least one of the pair of towers, the at least one apparatus includes a second housing member and a humidity sensor that is disposed at a first end of the second housing member for measuring humidity in ambient air. A temperature sensor is disposed at the first end of the second housing member for measuring ambient temperature.

An electronics portion is disposed in the second housing member and is electrically connected to the humidity sensor and the temperature sensor for computing at least one of a relative humidity and a dewpoint temperature.

A power means is electrically connected to the electronics portion, the humidity sensor and the temperature sensor for providing power to the apparatus, and a display means is electrically connected to the electronics portion and the power means for displaying at least one of such relative humidity and such dewpoint temperature as determined by said electronics portion. The display means is disposed at a second end of the second housing member.

OBJECTS OF THE INVENTION

It is, therefore, one of the primary objects of the present invention to provide a humidity indicator that is regenerative.

Another object of the present invention is to provide a humidity indicator that responds rapidly.

Still another object of the present invention is to provide a humidity indicator that is accurate.

Yet another object of the present invention is to provide a humidity indicator that can be used with air drying equipment.

An additional object of the present invention is to provide a humidity indicator that can provide a digital readout.

Also it is an object of the present invention to provide a humidity indicator that can provide a warning that the battery needs replacement.

In addition to the numerous objects and advantages of the present invention which have been described with some degree of particularity above, it should be both noted and understood that a number of other important objects and advantages of the battery powered humidity indicator will become more readily apparent to those persons who are skilled in the relevant art from the following more detailed description of the invention, particularly, when such detailed description is taken in conjunction with the attached drawing Figures and with the appended claims.

Figure 1:
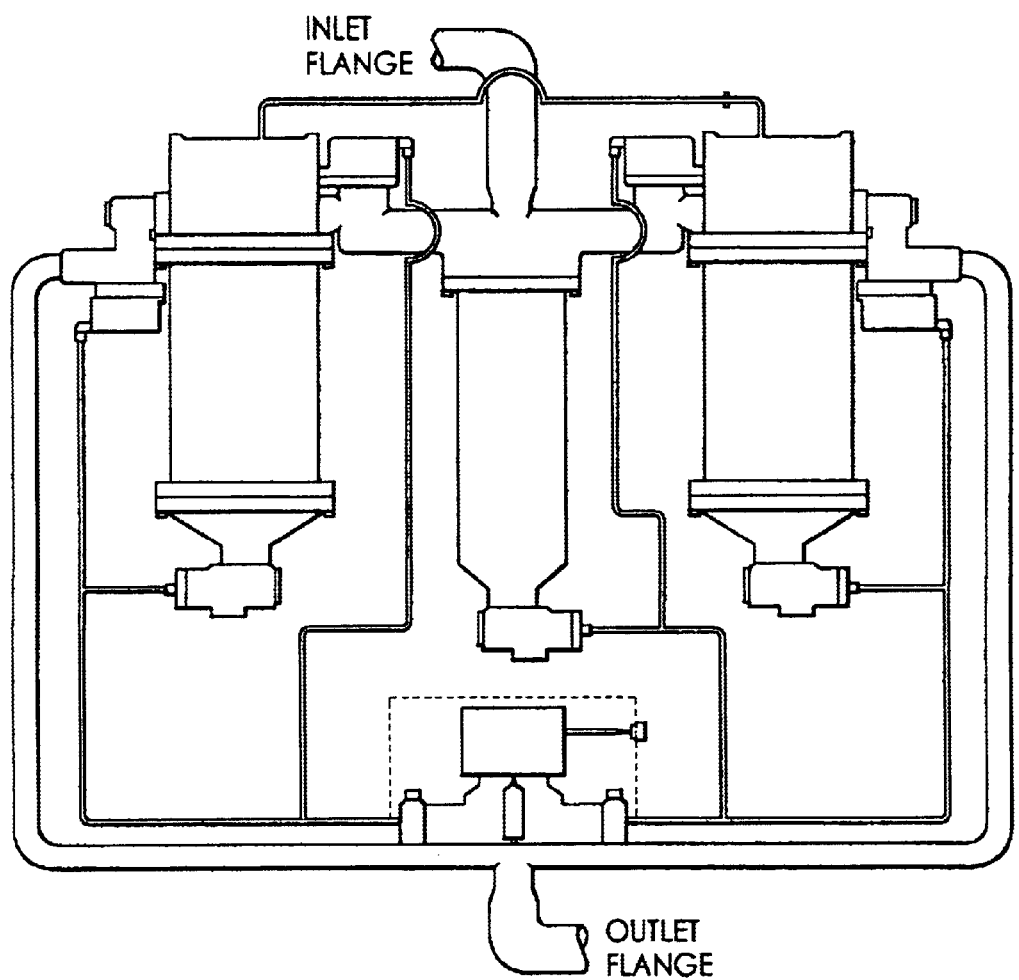
FIG. 1 is a schematic drawing of a prior art twin tower drying system.

BRIEF DESCRIPTION OF THE PRESENTLY PREFERRED AND VARIOUS ALTERNATE EMBODIMENTS OF THE INVENTION

Prior to proceeding to the more detailed description of the present invention, it should be noted that for the sake of clarity in understanding the invention, identical components with identical functions have been designated with identical reference numerals throughout the drawing Figures.

Figure 2:
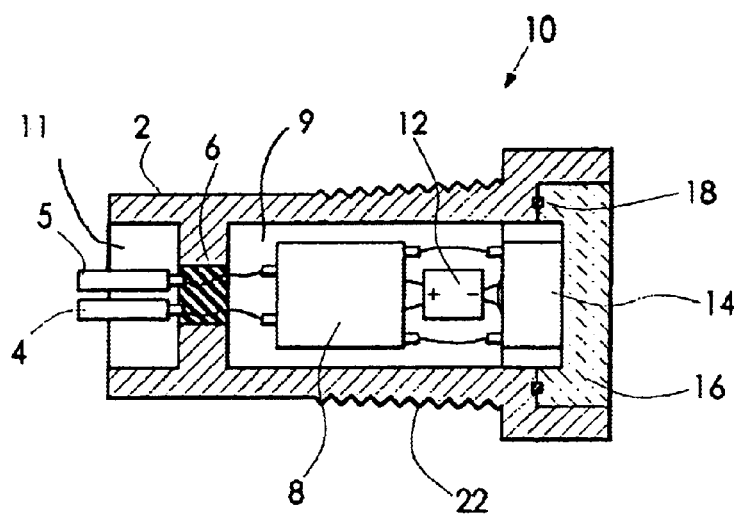
FIG. 2 is a schematic drawing of a battery powered humidity indicator of the present invention.
Figure 3:
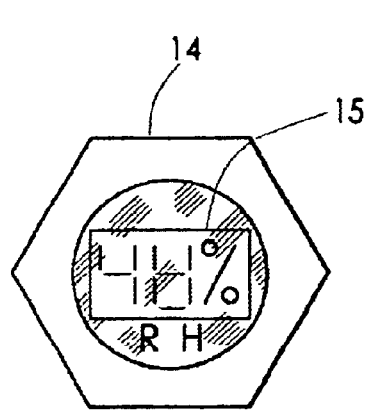
FIG. 3 is a drawing of the primary display showing relative humidity.
Figure 4:
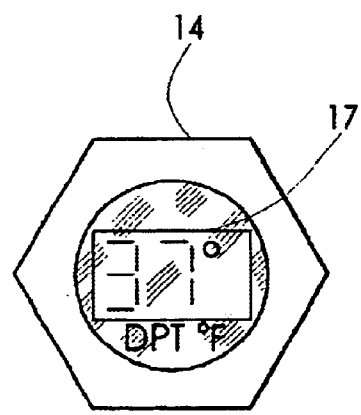
FIG. 4 is a drawing of an alternate display showing dew point temperature.

Reference is now made, more particularly, to FIGS. 2, 3 and 4. Illustrated therein are drawings showing an embodiment of the invention, a battery powered humidity indicator, generally designated 10. The battery powered humidity indicator 10 comprises a housing member 2. The housing member 2 has a first end and a second end. On the first end of the housing is disposed a sensor for measuring humidity 4. Closely adjacent to the humidity sensor 4 is a temperature sensor 5 which measures ambient temperature. The humidity sensor 4 measures the humidity of the surrounding atmosphere electrically. In a presently preferred embodiment of the invention, such housing member 2 further has a restriction and such connections from humidity sensor 4 and temperature sensor 5 are sealed in epoxy potting sealant 6 which seals off the inside of housing 2 from such ambient air.

As is clearly evident in FIG. 2 such housing member 2 has at least one substantially hollow portion 9. Preferably housing member 2 includes a second substantially hollow portion 11. There is an electronics portion 8 which is contained within such substantially hollow portion 9 of such housing member 2. Such electronics portion 8 is electrically connected to such humidity sensor 4 and such temperature sensor 5. The electronics portion 8 receives a humidity value from humidity sensor 4 and a temperature value from temperature sensor 5. From this data the electronics portion 8 calculates a relative humidity value and a dew point temperature. It is important that both a humidity value, representing the amount of moisture present in a fixed volume of air, and a temperature value be generated and transmitted to the electronics portion 8. These values are necessary in order to determine a relative humidity, since relative humidity is not only a function of the amount of moisture in the air but is also a function of temperature. It should be remembered that relative humidity represents a ratio of the amount of moisture actually present in the air to the amount of moisture in the air if the air were saturated. The amount of moisture that a given volume of air will hold varies with the temperature. The higher the temperature the more moisture the air will hold. For example, a cubic yard of air at a temperature of 86° F. may hold 1.42 cubic inches of water at saturation, the same cubic yard of air at 50° F. may only hold 0.44 cubic inches of water at saturation. Thus, it is important in the determination of relative humidity to have both a value for the amount of moisture in the air (humidity) as well as the temperature of the air.

These values of humidity and temperature are also necessary in order to calculate a dew point temperature. Dew point temperature is the temperature at which water vapor in the air begins to condensate. If saturated air is cooled, water will begin to condense. This is the dewpoint temperature.

The values that were calculated for relative humidity and dewpoint temperature are transmitted to a display means 14. In a preferred embodiment of the invention the display means 14 provides an LED digital readout. In a first embodiment of the invention, as is seen in FIG. 2, such display means 14 shows the relative humidity 15 displayed as a digital percentage value. In an alternate display, as seen in FIG. 3, display means 14 shows the dewpoint temperature 17 in degrees F. In an embodiment of the invention such LED readout of such display means 14 is covered with a crystal 16 to protect the display means 14 and the components inside the humidity indicator 10.

Such humidity indicator 10 further includes a power means 12 for supplying electrical power to the components. In a preferred embodiment of the invention such power means 12 is a battery. In the preferred embodiment such battery 12 is enclosed within housing 2 and provides the power needed for the operation of such humidity indicator 10. However, it is possible that the battery portion could be disposed other than being enclosed within housing 2. Such battery 12 is electrically connected to such electronics portion 8, humidity sensor 4, temperature sensor 5 and display means 14.

In an alternate embodiment of the invention a portion of such housing 2 has a threaded connection 22. Such threaded connection 22 is designed so the unit may be screwed into the threaded receptacle on an air dryer such as in a twin tower type air dryer such as is shown in FIG. 1.

The present invention is regenerative in that there is no dyed paper to content with and the apparatus can be used over and over again without making any changes. The response time of the present invention is estimated to be ≈1 to 5 seconds. Furthermore, the accuracy of the present invention is at least ±5 percent.

The only part of the unit that is not regenerative is the battery which has a finite life. However, an embodiment of the invention has the digital readout of the display such that the light flashes to indicate a low battery and replacement of the battery is a relatively simple operation. In this manner warning is given so that the battery could be replaced before a reading would be taken which could be in question. It is also possible that the battery could be replaced on a periodic basis during routine maintenance of such unit containing the battery powered humidity indicator.

In an alternate embodiment of the invention such humidity indicator 10 is provided in combination with an air drying system such as the twin tower type air dryer as is shown in FIG. 1. Some examples of air drying systems are found in U.S. Pat. No. 5,961,698 and U.S. Pat. No. 5,715,621. These patents are assigned to the Assignee of the present invention and their teachings are incorporated into the present document by reference thereto.

The improvement in the twin tower air dryer is the inclusion of the battery powered humidity indicator 10 described previously. Such air drying system has a first housing member, an air inlet manifold and an air outlet manifold disposed in the first housing member, a pair of towers disposed in the first housing, a first one of a pair of towers serving as a drying tower fluidly connected to the air inlet manifold and the air outlet manifold whenever a second one of the pair of towers is being regenerated and the second one of the pair of towers serving as a drying tower when the first one of the pair of towers is being regenerated. The battery powered humidity indicator 10 is disposed in the housing of such air drying system.

While a number of presently preferred and various alternative embodiments of the present invention have been described in detail above, various other adaptations and modifications of the battery powered humidity indicator may be made by those persons who are skilled in the relative art without departing from either the spirit of the invention or the scope of the appended claims.

We claim:

1. An apparatus used to measure relative humidity, said apparatus comprising:

(a) a housing member having at least one substantially hollow portion, (b) a humidity sensor disposed at a first end of said housing member for measuring humidity in ambient air, (c) a temperature sensor disposed at said first end of said housing member for measuring ambient temperature, (d) an electronics portion disposed within said at least one substantially hollow portion of said housing member and electrically connected to said humidity sensor and said temperature sensor for computing at least one of a relative humidity and a dewpoint temperature, (e) a power means electrically connected to said electronics portion, said humidity sensor and said temperature sensor for providing power to said apparatus, and (f) a display means electrically connected to said electronics portion and with said power means for displaying at least one of such relative humidity and such dew point as determined by said electronics portion, said display means disposed at a second end of said housing member.

2. An apparatus used to measure relative humidity, according to claim 1, wherein said apparatus further includes a means for protecting said display means.

3. An apparatus used to measure relative humidity, according to claim 2, wherein said means for protecting said display means includes a crystal positioned over said display means.

4. An apparatus used to measure relative humidity, according to claim 1, wherein at least a portion of an exterior surface of said housing of said apparatus is threaded.

5. An apparatus used to measure relative humidity, according to claim 1, wherein said display means is an LED readout.

6. An apparatus used to measure relative humidity, according to claim 5, wherein said LED readout displays relative humidity as a digital percentage.

7. An apparatus used to measure relative humidity, according to claim 5, wherein said LED readout displays a digital dewpoint temperature in degrees Fahrenheit.

8. An apparatus used to measure relative humidity, according to claim 1, wherein said power means is a battery.

9. An apparatus used to measure relative humidity, according to claim 8, wherein said battery is disposed within said housing.

10. An apparatus used to measure relative humidity, according to claim 1, wherein connections from said humidity sensor and said temperature sensor are sealed in epoxy potting sealant for sealing an inside of said housing from ambient air.

11. In combination with an air drying system having a first housing member, an air inlet manifold and an air outlet manifold disposed in said first housing member, a pair of towers disposed in said housing, a first one of said pair of towers serving as a drying tower fluidly connected to said air inlet manifold and said air outlet manifold whenever a second one of said pair of towers is being regenerated and said second one of said pair of towers serving as a drying tower when said first one of said pair of towers is being regenerated, the improvement comprising:

at least one apparatus disposed in said housing for measuring relative humidity, said at least one apparatus fluidly connected to said air inlet manifold, said air outlet manifold and said at least one of said pair of towers, said at least one apparatus including:

(a) a second housing member having at least one substantially hollow portion, (b) a humidity sensor disposed at a first end of said second housing member for measuring humidity in ambient air, (c) a temperature sensor disposed at said first end of said second housing member for measuring ambient temperature, (d) an electronics portion disposed within said at least one substantially hollow portion of said second housing member and electrically connected to said humidity sensor and said temperature sensor for computing at least one of a relative humidity and a dewpoint temperature, (e) a power means electrically connected to said electronics portion, said humidity sensor and said temperature sensor for providing power to said apparatus, and (f) a display means electrically connected to said electronics portion and with said power means for displaying at least one of such relative humidity and such dewpoint temperature as determined by said electronics portion, said display means disposed at a second end of said second housing member.

12. The combination, according to claim 11, wherein said apparatus further includes a means for protecting said display means.

13. The combination, according to claim 12, wherein said means for protecting said display means includes a crystal positioned over said display means.

14. The combination, according to claim 11, wherein at least a portion of an exterior surface of said housing of said apparatus is threaded.

15. The combination, according to claim 11, wherein said display means is an LED readout.

16. The combination, according to claim 15, wherein said LED readout displays relative humidity as a digital percentage.

17. The combination, according to claim 15, wherein said LED readout displays a digital dewpoint temperature in degrees Fahrenheit.

18. The combination, according to claim 11, wherein said power means is a battery.

19. The combination, according to claim 18, wherein said battery is disposed within said housing.

20. The combination, according to claim 11, wherein connections from said humidity sensor and said temperature sensor are sealed in epoxy potting sealant for sealing an inside of said housing from ambient air.

* * * * *